(12) United States Patent
Steele et al.

(10) Patent No.: US 11,400,187 B2
(45) Date of Patent: Aug. 2, 2022

(54) THERAPEUTIC NANOPARTICLES FOR TREATING VASCULAR DISEASES

(71) Applicant: Medtronic Vascular, Inc., Santa Rosa, CA (US)

(72) Inventors: Bradley Steele, Plymouth, MN (US); Simone D'Onofrio, Brescia (IT); Massimo Morero, Turin (IT); Federica Bellucci, Alessandria (IT); Cassandra Morris, Plymouth, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 559 days.

(21) Appl. No.: 16/160,669

(22) Filed: Oct. 15, 2018

(65) Prior Publication Data

US 2019/0111187 A1    Apr. 18, 2019

Related U.S. Application Data

(60) Provisional application No. 62/572,870, filed on Oct. 16, 2017.

(51) Int. Cl.

| | | |
|---|---|---|
| *A61K 9/00* | (2006.01) |
| *A61K 9/16* | (2006.01) |
| *A61F 2/82* | (2013.01) |
| *A61M 25/00* | (2006.01) |
| *A61L 29/16* | (2006.01) |
| *A61P 5/44* | (2006.01) |
| *A61K 31/56* | (2006.01) |
| *A61K 31/337* | (2006.01) |
| *A61L 31/10* | (2006.01) |
| *A61P 29/00* | (2006.01) |
| *A61L 31/16* | (2006.01) |
| *A61K 31/436* | (2006.01) |
| *A61L 29/08* | (2006.01) |
| *A61M 25/10* | (2013.01) |

(52) U.S. Cl.
CPC ............... *A61L 29/16* (2013.01); *A61F 2/82* (2013.01); *A61K 9/0009* (2013.01); *A61K 9/167* (2013.01); *A61K 9/1676* (2013.01); *A61K 31/337* (2013.01); *A61K 31/436* (2013.01); *A61K 31/56* (2013.01); *A61L 29/085* (2013.01); *A61L 31/10* (2013.01); *A61L 31/16* (2013.01); *A61M 25/0045* (2013.01); *A61M 25/104* (2013.01); *A61P 5/44* (2018.01); *A61P 29/00* (2018.01); *A61F 2210/009* (2013.01); *A61F 2210/0076* (2013.01); *A61F 2250/0067* (2013.01); *A61L 2300/41* (2013.01); *A61L 2300/416* (2013.01); *A61L 2300/606* (2013.01); *A61L 2300/624* (2013.01); *A61L 2400/12* (2013.01); *A61L 2420/04* (2013.01); *A61L 2420/08* (2013.01); *A61M 2025/0057* (2013.01); *A61M 2025/0058* (2013.01); *A61M 2025/105* (2013.01); *A61M 2025/1075* (2013.01); *A61M 2025/1088* (2013.01); *A61M 2205/0238* (2013.01); *A61M 2205/0288* (2013.01)

(58) Field of Classification Search
None
See application file for complete search history.

(56) References Cited

U.S. PATENT DOCUMENTS

| | | | |
|---|---|---|---|
| 8,119,153 B2 | 2/2012 | Weber | |
| 2007/0055364 A1* | 3/2007 | Hossainy | A61L 31/16 623/1.38 |
| 2009/0061010 A1 | 3/2009 | Zale et al. | |
| 2010/0204674 A1* | 8/2010 | Forbes | A61N 2/00 604/500 |
| 2011/0143993 A1 | 6/2011 | Langer et al. | |
| 2012/0156135 A1* | 6/2012 | Farokhzad | A61K 47/6911 424/9.1 |
| 2013/0284310 A1 | 10/2013 | Peterson et al. | |

(Continued)

FOREIGN PATENT DOCUMENTS

| | | |
|---|---|---|
| EP | 0710261 A1 | 8/1996 |
| WO | WO 95/03357 A1 | 2/1995 |

(Continued)

OTHER PUBLICATIONS

Chan et al., "PLGA-lecithin-PEG core-shell nanoparticles for controlled drug delivery," *Biomaterials*, 2009; 30:1627-1634.

(Continued)

*Primary Examiner* — Robert T. Crow
*Assistant Examiner* — John P Nguyen
(74) *Attorney, Agent, or Firm* — Mueting Raasch Group

(57) ABSTRACT

A variety of nanoparticles or microparticles may be used to treat diseases such as restenosis or blood clots. For example, a nanoparticle or microparticle may include a core having a biodegradable polymer, an exterior having hydrophilic moieties, and a therapeutic agent. The nanoparticles may include targeting moieties that target the nanoparticle or microparticle to an arterial lesion. The nanoparticle or microparticle may include an exterior shell around the core to increase stability of the nanoparticle or microparticle. The nanoparticle or microparticle may include a magnetic particle to allow targeted delivery of the nanoparticle or microparticle via a magnetic field. The nanoparticles or microparticles may be coated on a medical device, such as a catheter balloon or a stent, or may be delivered systemically or locally to patients in need thereof.

21 Claims, 3 Drawing Sheets

(56) References Cited

U.S. PATENT DOCUMENTS

2016/0193349 A1* 7/2016 Heller ................ A61K 47/643
                                                        424/1.11

FOREIGN PATENT DOCUMENTS

| WO | WO 2010/068866 A2 | 6/2010 |
| WO | WO 2010/068866 A3 | 10/2010 |

OTHER PUBLICATIONS

European Search Report for Application No. EP 18199908.7, dated Feb. 25, 2019, 13 pages.
Zhang et al., "Lipid-stabilized polymeric nanoparticles for targeted drug delivery," Conference Proceedings, 2007 Aiche Annual Meeting, Nov. 4-9, 2007, Salt Lake City, Utah; 1 page.

* cited by examiner

THERAPEUTIC NANOPARTICLES FOR TREATING VASCULAR DISEASES

RELATED APPLICATION

This application claims the benefit of U.S. Provisional Application No. 62/572,870, filed Oct. 16, 2017, the disclosure of which is incorporated by reference herein in its entirety.

FIELD

The present disclosure relates to nanoparticles or microparticles for treating vascular diseases, such as restenosis or clotting.

BACKGROUND

Vascular atherosclerotic lesions that create arterial luminal narrowing are typically treated in angioplasty procedures via catheters provided with an inflatable balloon. The catheter is advanced, typically following a guidewire, to an opening within the atherosclerotic lesion of the narrowed artery. Once the inflatable balloon has been arranged at the artery narrowing, it may be inflated and deflated, sometimes repeatedly. The inflation, with successive deflation, of the inflatable balloon within the artery can reduce the extent of the arterial luminal narrowing, and restore a suitable blood flow.

In many cases, patients develop a re-narrowing of the vessel lumen at the intervention point within a few months. Such re-narrowing, or restenosis, is due to a cell hyperproliferation process, particularly of the vascular smooth muscle cells, and may be due to the dilating action caused by the inflatable balloon.

Inflatable balloons or stents can be coated with a drug having anti-proliferative action to prevent or retard restenosis. Among the therapeutics agents usually employed to such aim, paclitaxel (taxol) has proved to be particularly efficient.

However, with current therapies the paclitaxel delivered by the balloon catheter to the wall of the vessel drops below an effective concentration after a period of time. For example, the paclitaxel may be present on the vessel wall in an effective anti-proliferative concentration for about 6 months following treatment. It may be desirable to increase the amount of therapeutic agent, such as paclitaxel, that is delivered to and is retained by the vessel and the length of time that the therapeutic agent is present at the vessel wall in an effective concentration.

Also, blood clots can significantly reduce blood flow in arteries and veins, leading to ischemic events. Current treatments rely on relatively high systemic doses of anti-clotting and thrombolytic agents to disrupt the clots. It may be desirable to target the delivery of anti-clotting and/or thrombolytic agents to blood clots in order to reduce the systemic dosage required to achieve sufficient disruption of the blood clot.

SUMMARY

The present disclosure describes, among other things, nanoparticles or microparticles for delivering therapeutic agents to patients in need thereof. The nanoparticles or microparticles may contain therapeutic agents to prevent restenosis or to disrupt blood clots. The nanoparticles or microparticles may be coated on a medical device, such as a catheter balloon or a stent, or may be delivered systemically or locally to patients in need thereof.

The nanoparticles or microparticles may comprise a biodegradable polymer that releases a therapeutic agent at suitable rate. The size and composition of the nanoparticle or microparticle may be adjusted to tune the release rate of the therapeutic agents.

In some embodiments, the nanoparticle or microparticle includes a copolymer having a hydrophobic portion and a hydrophilic portion. For example, the copolymer may comprise a hydrophilic block and a hydrophobic block. The copolymer may self-assemble into the nanoparticle or microparticle when placed in an aqueous environment such that the hydrophobic portions are located at the core of the nanoparticle or microparticle and the hydrophilic portions are located at the exterior of the nanoparticle or microparticle. The therapeutic agents may be incorporated into the nanoparticle or microparticle during self-assembly, or may be incorporated into the nanoparticle or microparticle in any other suitable manner.

The nanoparticles or microparticles may be targeted to a particular tissue, such as a blood clot, or lesioned vascular tissue in enhance the concentration of the therapeutic agent at the targeted tissue relative to non-targeted tissue. The nanoparticles or microparticles may comprise magnetic particles to enhance directed delivery of the nanoparticles or microparticles to an appropriate tissue via a magnetic field.

In various embodiments described herein, the nanoparticle or microparticle may comprise a hydrophobic polymer core and a lipid monolayer. The lipid monolayer may be formed from a phospholipid or other lipid molecule having, or modified to have, at least one hydrophilic moiety. For example, a polyethylene glycol (PEG) moiety may be attached to a lipid molecule to form a hydrophilic portion of the lipid monolayer. The hydrophobic portion of the lipid monolayer may be incorporated in the core of the nanoparticle or microparticle and the hydrophilic moiety may be located at the exterior of the nanoparticle or microparticle. The nanoparticles or microparticles may contain a therapeutic agent for preventing restenosis, such as an anti-proliferative agent and/or an anti-inflammatory agent. The nanoparticles or microparticles may be coated on a medical device, such as a balloon catheter or stent, which may be tracked to a target location within a vessel, such as a site of a lesion, for delivery. Alternatively, the nanoparticles or microparticles may be administered systemically, such as intravenously, to a patient, or locally such as via local intravascular injection with or without occlusion balloons.

In various embodiments described herein, nanoparticles or microparticles include a polymer forming a core of the nanoparticle or microparticle and include a targeting moiety exposed an external surface, where the targeting moiety interacts with a component of a vascular lesion. For example, the targeting moiety may interact with activated platelets or collagen. The nanoparticles or microparticles may contain a therapeutic agent for preventing restenosis, such as an anti-proliferative agent and/or an anti-inflammatory agent. The nanoparticles or microparticles may be coated on a medical device, such as a balloon catheter or stent, which may be tracked to a target location within a vessel, such as a site of a lesion, for delivery. Alternatively, the nanoparticles or microparticles may be administered systemically, such as intravenously, to a patient, or locally such as via local intravascular injection with or without occlusion balloons.

In various embodiments described herein, nanoparticles or microparticles include an exterior shell surrounding a polymeric nanoparticle or microparticle core. The exterior shell increases the stability of the nanoparticle or microparticle to increased temperature, increased humidity, solvents, and aging. The shell may also decrease the rate at which the nanoparticle or microparticle releases a therapeutic agent. The shell may serve to block the effect of outside factors, by acting as a sacrificial layer, or both. The shell may reduce the rate of degradation of the nanoparticle or microparticle when the nanoparticle or microparticle is exposed to chemicals, enhance stability during sterilization, and increase shelf-life of the nanoparticle or microparticle. The shell may enhance the stability of the nanoparticle or microparticle during processing, handling, sterilization, delivery to the patient, and the like.

In various embodiments described herein, a nanoparticle or microparticle includes an anti-coagulation agent or a thrombolytic agent. The nanoparticle or microparticle may further comprise a targeting moiety to direct the nanoparticle or microparticle to blood clots. Examples of moieties that target activated platelet targeting moieties, moieties that target collagen, moieties that target fibrin, and moieties that target one or more clotting factors.

In various embodiments described herein, a nanoparticle or microparticle includes a therapeutic agent and a magnetic particle. The magnetic particle may be directed to a particular location in a patient by magnetic field internal or external to the patient. For example, the nanoparticle or microparticle may be attracted to a magnetic field applied by an electromagnet of a medical device as the device is tracked through the patient's vasculature. Once the nanoparticle or microparticle is delivered to a target intravascular site, current to the electromagnet may be turned off to release the nanoparticles or microparticles from the device. In addition or alternatively, an external magnetic field may be applied to direct the nanoparticles or microparticles containing the magnetic particles to a target tissue.

Advantages of one or more of the various embodiments presented herein over prior nanoparticles or microparticles, treatment modalities, or the like will be readily apparent to those of skill in the art based on the following detailed description when read in conjunction with the accompanying drawings.

Figure 1:
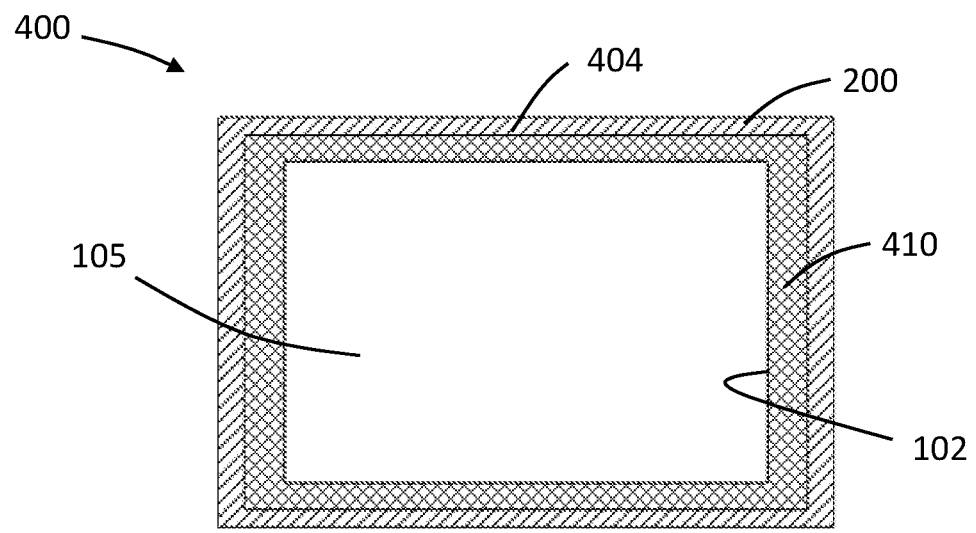
FIG. 1 is a schematic sectional view of an embodiment of a medical device having a coating comprising a nanoparticle or microparticle for releasing a therapeutic agent.

The schematic drawings presented herein are not necessarily to scale.

DETAILED DESCRIPTION

In the following detailed description, reference is made to the accompanying drawings that form a part hereof, and in which are shown by way of illustration several specific embodiments of devices, systems and methods. Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components. It is to be understood that other embodiments are contemplated and may be made without departing from the scope or spirit of the present disclosure. The following detailed description, therefore, is not to be taken in a limiting sense.

This disclosure relates to, among other things, nanoparticles or microparticles for delivering therapeutic agents to patients in need thereof. In various embodiments, the nanoparticles or microparticles contain one or more therapeutic agents to prevent restenosis or to disrupt blood clots. The nanoparticles or microparticles may be coated on a medical device, such as a catheter balloon or a stent, or may be delivered systemically or locally in any suitable manner to patients in need thereof.

The nanoparticles or microparticles may comprise a biodegradable polymer that releases a therapeutic agent at suitable rate. Examples of suitable biodegradable polymers that may be used include poly($\alpha$-esters); polyglucolide (PGA); polylactide (PLA); poly(lactide-co-glycolide) (PLGA); polyhydroxyalkanoates such as poly(3-hydroxybutyrate) (PHB); polycaprolactone (PCL); poly(propylene fumarate) (PFF); polyanhydrides such as poly(sebacic anhydride) (pSA); polyacetals such as polyoxymethylene; poly (ortho esters); polycarbonates such as poly(trimethylene carbonate) (PTMC); polyurethanes; polyphosphazenes; polyphosphoesters; and combinations thereof.

The size and composition of the nanoparticle or microparticle may be adjusted to tune the release rate of the therapeutic agents.

In various embodiments, the nanoparticles or microparticles comprise PLGA. The ratio of lactide to glycolide may be varied to control the rate of degradation of the nanoparticle or microparticle. For example, the molar ratio of lactide to glycolide may vary from about 50:50 to about 90:10. The rate of degradation may be slowed as the percentage of lactide to glycolide increases. Thus, the release rate of the therapeutic agent may be tuned by altering the ratio of lactide to glycolide.

The nanoparticles or microparticles may be of any suitable size. For example, the nanoparticles or microparticles may have a size from about 10 nm to about 50,000 nanometers, such as from about 20 nm to about 1,000 nanometers, or from about 50 nm to about 500 nm. The size of the nanoparticles or microparticles may be dependent on the molecular weight of the polymer or other constituents of the nanoparticle or microparticle. For example, the nanoparticle or microparticle may comprise PLGA having a molecular weight (Mw) from about 7 kDa to about 240 kDa.

The nanoparticle or microparticle may comprise a core and an exterior. The core may be formed from the polymer. For example, the core may be formed by PLGA.

The therapeutic agent may be in the core of the nanoparticle or microparticle, tethered to the exterior, or between the core and the exterior of the nanoparticle or microparticle. The location of the therapeutic agent in the nanoparticle or microparticle and the mechanism of incorporation of the therapeutic agent into the nanoparticle or microparticle may depend on the nature of the polymer employed, the nature of the therapeutic agent, and other constituents of the nanoparticle or microparticle.

In some embodiments, the polymer includes a hydrophobic portion and a hydrophilic portion or is modified to contain a hydrophobic portion and a hydrophilic portion. For example, the polymer may be a block copolymer that comprises a hydrophilic block and a hydrophobic block. The copolymer may self-assemble into the nanoparticle or microparticle when placed in an aqueous environment such that the hydrophobic portions are located at the core of the nanoparticle or microparticle and the hydrophilic portions are located at the exterior of the nanoparticle or microparticle. For example, the nanoparticle or microparticle may comprise a block copolymer where the hydrophobic block comprises PLGA and a hydrophilic block comprising, for example, polyethylene glycol (PEG) a polysaccharide, or the like.

As another example, a hydrophilic moiety may be attached to a hydrophobic polymer, such as PLGA, to form an amphiphilic molecule that may self-assemble into a nanoparticle or microparticle.

In some embodiments, the nanoparticle or microparticle comprises a first hydrophobic polymer, such as PLGA, and a second amphiphilic polymer or compound, such as a block copolymer, oleate salts, vitamin E, or the like. The first polymer and second polymer or compound may self-assemble into nanoparticles or microparticles when placed in water, with the first polymer and the hydrophobic portion of the second polymer or compound forming the exterior of the nanoparticle or microparticle. The percentage of the first polymer and second polymer or compound, as well as the composition of the polymers and compounds, may be varied to control the rate of degradation and the rate of release of the therapeutic agent.

As used herein, a "hydrophilic" polymer or compound is a polymer or compound that is more soluble in water than in octanol. A "hydrophobic" polymer or compound is a polymer or compound that is less soluble in octanol than in water. In some embodiments, a hydrophilic polymer has a solubility in water of 10 milligrams per liter or greater. In some embodiments, a "hydrophobic" polymer has a solubility in water of 1 milligram per liter or less. The precise chemical structure of a polymer or block is not as important as the degree or hydrophilicity or hydrophobicity because the nanoparticles or microparticles preferably self-assemble such that hydrophobic components cluster or hydrophilic components cluster under conditions employed for forming the nanoparticles or microparticles. One of skill in the art of self-assembled nanoparticle or microparticle synthesis will readily appreciate and understand what polymers are considered hydrophilic and what polymers are considered hydrophobic.

In various embodiments, the nanoparticle or microparticle may comprise a lipid monolayer. The lipid monolayer may be formed from a phospholipid or other lipid molecule having, or modified to have, at least one hydrophilic moiety. The lipid portion may be incorporated in the core of the nanoparticle or microparticle and the hydrophilic moiety may be located at the exterior of the nanoparticle or microparticle. Examples of suitable lipids that may be employed to form the lipid monolayer include phosphatidylcholine (PC), 1,2-dilauroyl-sn-glycero-3-phosphocholine (DLPC), 1,2-distearoylsn-glycero-3-phosphoethanolamine (DSPE), cholesterol, myristic acid, stearic acid, 1,2-dipalmitoyl-sn-glycero-3-phosphocholine (DPPC), and the like. Examples of hydrophobic moieties that may be attached to lipid molecules include PEG and the like.

The therapeutic agents, particularly if the therapeutic agents are hydrophobic, may be incorporated into the core during self-assembly of the nanoparticle or microparticle. In addition or alternatively, the therapeutic agents may be tethered to the polymer or other molecule tethered to the polymer via a cleavable linker using suitable chemistry, such as click chemistry; N-hydroxysuccinimide (NHS) coupling with for example, 1-ethyl-3-(3-dimethylaminopropyl)-carbodimide (EDC) (NHS/EDC coupling); or the like.

The nanoparticles or microparticles may comprise any suitable therapeutic agent. For example, the nanoparticle or microparticle may include one or more of heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a calcium channel blocker, a nitrate, nitric oxide, a nitric oxide promoter or another vasodilator; an antimicrobial agent or antibiotic; aspirin, ticlopdine or another antiplatelet agent; colchicine or another antimitotic, or another microtubule inhibitor; cytochalasin or another actin inhibitor; a remodeling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anticancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; a radiotherapeutic agent; a peptide, a protein, an enzyme, an extracellular matrix component, a cellular component or another biologic agent; captopril, enalapril or another angiotensin converting enzyme (ACE) inhibitor; alphatocopherol, superoxide dismutase, deferoxyamine, a 21-aminosteroid (lasaroid) or another free radical scavenger, iron chelator or antioxidant; and angiopeptin.

In various embodiments, the nanoparticles or microparticles comprise one or more anti-restenosis therapeutic agent. For example, the nanoparticles or microparticles may include anti-proliferative agent, an anti-mitotic agent, or the like. One or more taxol or limus-derivative may be employed as an anti-restenosis therapeutic agent. Some non-limiting examples of anti-restenosis agents are paclitaxel, doxetaxel, sitolimus, rapamycin, everolimus, zotarolimus, and the like.

In some embodiments, the nanoparticles or microparticles comprise an anti-inflammatory agent. Anti-inflammatory agents, such as steroid anti-inflammatory agents and non-steroidal anti-inflammatory agents may be used. For example, anti-inflammatory agents may include glucocorticoids or cyclooxygenase (COX) inhibitors.

In some embodiments, the nanoparticles or microparticles comprise a therapeutic agent to disrupt a blood clot, such as a thrombolytic agent. Non-limiting examples of thrombolytic agents include tissue plasminogen activator (TPA), streptokinase, urokinase, tenecteplase, rokinase, reteplase, anistreplase, and the like.

Unless content clearly dictates otherwise, general reference to a therapeutic agent in the present disclosure includes reference to salts of the agent, hydrates of the agent, polymorphs of the agent, isomers of the agent (including constitutional isomers and stereoisomers such as enantiomers and diasteriomers), and the like.

A therapeutic agent may be present in the nanoparticle or microparticle at any suitable concentration. For example, an anti-inflammatory agent may be present in the nanoparticle or microparticle at a concentration from about 0.0001% to about 40% by weight of the nanoparticle or microparticle.

Preferably, the therapeutic agent and the concentration of nanoparticle or microparticle delivered to a patient are delivered in a therapeutically effective amount. As used herein, "therapeutically effective amount" means an agent in an amount capable of inducing a therapeutic or preventive effect against the disease being treated or prevented. For example, if the disease being treated or prevented is restenosis of vascular tissue, the one or more agents present in the nanoparticles or microparticles may be present in an amount effective to treat or prevent restenosis of the treated vascular tissue in the patient.

More than one therapeutic agent may be employed in the same or different nanoparticles or microparticles to achieve release profiles as desired. In some embodiments, the same therapeutic agent is associated with different nanoparticles or microparticles.

The nanoparticles or microparticles described herein include one or more moieties that target the nanoparticles or microparticles to target tissue locations or cells. As used herein, "targeting" a nanoparticle or microparticle to a target location means that the nanoparticle or microparticle accumulates at the target location relative to other locations at a greater concentration than a substantially similar non-targeted nanoparticle or microparticle. A substantially similar non-target nanoparticle or microparticle includes the same components in substantially the same relative concentration (e.g., within about 5%) as the targeted nanoparticle or microparticle, but lacks a targeting moiety.

Any suitable targeting moiety may be employed. For example, the targeting moiety may target the nanoparticles or microparticles to vascular lesions, such as arterial lesions. Fucoidan may be employed to target activated platelets, may be present at vascular lesions and recently treated vessels (e.g., vessels treated via angioplasty). A collagen binding peptidoglycan, such as dermatan sulfate-RRANAALK-AGELYKSILYGC (SEQ ID NO: 1) (DS-SILY) may be employed to target collagen, which may be present at recently treated arterial lesions.

In some embodiments, the targeting moiety may target the nanoparticles or microparticles to blood clots, such as forming or recently formed blood clots. Fucoidan and DS-SILY may be suitable blood clot-targeting agents. Fibrin-targeting peptides, such as CREKA (SEQ ID NO: 2), may be incorporated into the nanoparticle or microparticle to blood clots.

The targeting moieties may be tethered to the core in any suitable manner, such as binding to a molecule that forms part of the core or to a molecule that is bound to the core. In embodiments, a targeting moiety is bound to a hydrophilic polymer that is bound to a hydrophobic polymer that forms part of the core. In embodiments, a targeting moiety is bound to a hydrophilic portion of a block copolymer having a hydrophobic block that forms part of the core.

The targeting moieties may be bound to any suitable portion of a polymer. In embodiments, the targeting moieties are attached to a terminal end of a polymer. In embodiments, the targeting moieties are bound to the backbone of the polymer, or a molecule attached to the backbone, at a location other than a terminal end of the polymer. More than one targeting moiety may be bound to a given polymer. In embodiments, the polymer is a dendritic polymer having multiple terminal ends and the targeting moieties may be bound to more than one of terminal ends.

The polymers, or portions thereof, to which the targeting moieties are bound may contain, or be modified to contain, appropriate functional groups, such as —OH, —COOH, —NH2, —SH, —N3, —Br, —Cl, —I, or the like, for reaction with and binding to the targeting moieties that have, or are modified to have, suitable functional groups.

In various embodiments, the nanoparticles or microparticles include an exterior shell to surrounding the polymeric core. The exterior shell may increase the stability of the nanoparticle or microparticle to one or more of increased temperature, increased humidity, solvents, and aging. The shell may also decrease the rate at which the nanoparticle or microparticle releases a therapeutic agent. The shell may serve to block the effect of outside factors, by acting as a sacrificial layer, or both. The shell may reduce the rate of degradation of the nanoparticle or microparticle when the nanoparticle or microparticle is exposed to chemicals, enhance stability during sterilization, and increase shelf-life of the nanoparticle or microparticle. The shell may prevent or delay penetration of water into the particle until the particle is delivered to a patient. The shell may enhance the stability of the nanoparticle or microparticle during processing, handling, sterilization, delivery to the patient, and the like.

Any suitable shell may be employed. For example, the shell may comprise a layer of PLGA that has a high lactide composition and high molecular weight. The molar ratio of lactide to glycolide may be, for example, from about 75:25 to about 90:10. The molecular weight (Mw) may be 100 kDa or greater, such as from about 100 kDa to about 240 kDa. The shell may comprise a wax such as carbowax 8000; a blend of hydrophilic and hydrophobic polymers such as Medtronic Inc.'s BioLinx™ polymer; paralyne, a polysaccharide such as cellulose or pectin, a lipophilic layer, or a layer of polylactic acid (PLA).

In various embodiments, the nanoparticles or microparticles include a magnetic particle. The magnetic particle may be directed to a particular location in a patient by magnetic field internal or external to the patient. Any suitable magnetic particle may be employed. In some embodiments, the magnetic particle comprises iron oxide. The magnetic particle may be incorporated into the nanoparticle or microparticle in any suitable manner. For example, the magnetic particle may be in the core of the nanoparticle or microparticle or may be tethered to one or more constituent of the nanoparticle or microparticle, for example as described above regarding therapeutic agents.

In some embodiments, the nanoparticles or microparticles may be attracted to a magnetic field applied by an electromagnet of a medical device as the device is tracked through the patient's vasculature. Once the nanoparticle or microparticle is delivered to a target intravascular site, current to the electromagnet may be turned off to release the nanoparticles or microparticles from the device. In addition or alternatively, an external magnetic field may be applied to direct the nanoparticles or microparticles containing the magnetic particles to a target tissue.

In various embodiments, nanoparticles or microparticles are disposed on a medical device that may be tracked through the vasculature to a target site, where the nanoparticles or microparticles may be locally delivered. In some embodiments, the nanoparticles or microparticles are locally delivered to the vasculature via injection. In some embodiments, local injection into the vasculature may include infusion between occlusion balloons or injection into a vessel wall. In some embodiments, the nanoparticles or microparticles are delivered systemically. For example, the nanoparticles or microparticles may be delivered intravenously or intramuscularly.

When the nanoparticles or microparticles are coated on a medical device, the coating preferably provides for release and bioavailability of a therapeutically effective amount of the therapeutic agent when the coating contacts tissue at the site of intervention. The coating may include any suitable number of layers. The therapeutic agent-containing nanoparticles or microparticles may be intermixed with other components of the coating and applied as a single layer. In some embodiments, a layer comprising therapeutic agent-containing nanoparticles or microparticles is applied to the medical device and a layer, such as a polymeric layer, is applied on top of the nanoparticle-containing or microparticle-containing layer. In some embodiments, a layer, for example comprising a polymer, is applied to the medical device and a layer comprising the nanoparticles or microparticles is applied on top of the previously applied layer.

In general, a coating layer may be disposed on the medical device or on a coating layer disposed on the medical device in any suitable manner. For example, a solution comprising the components of the layer, such as the nanoparticle or microparticle may be coated on the medical device by dipping the medical device in the solution, the solution may be sprayed on the medical device, or the solution may be deposited on the device with, for example, a syringe, micropipette, or other similar dispensing device.

If the medical device comprises, for example, an inflatable balloon or an expandable stent, the solution may be applied when the inflatable balloon is inflated or the stent is expanded, or when the balloon is in a folded condition or the sent is contracted. If the medical device comprises an inflatable balloon and the coating is applied when the inflatable balloon is in the folded condition, the solution may penetrate under the folds by capillary action or may be applied by, for example, micro-nozzles under the folds. If the medical device comprises a stent, the stent may be coated by filling the stent via capillary action as described in, for example, U.S. Patent Application Publication No. 2013/0284310 or may be coated in any other suitable manner.

One or more coatings of the solution may be applied to the medical device or other coating layer. The solvent may be allowed to evaporate under ambient conditions, under heated conditions, under vacuum drying, or heating and vacuum drying. The medical device or underlying coating layer may be fully or partially coated with the layer or subsequent layer.

The coatings described herein may be applied to any suitable medical device. Preferably, the medical device comprises a coated portion deliverable through a blood vessel of a patient. For example, the medical device may comprise an inflatable balloon or a stent, such as a self-expanding stent or a balloon expandable stent. The medical device may comprise a balloon catheter comprising an inflatable balloon.

Any suitable inflatable medical inflatable balloon may be coated with a nanoparticle or microparticle coating described herein. The inflatable balloons may be compliant, semi-compliant or non-compliant. The inflatable balloons may be formed from any suitable material. For example, the inflatable balloons may be formed of polyamides, polyethylene terephathalate (PET), polyurethane, latex, silicone, polyethylene (PE), polypropylene (PP), polyetherimide (PEI), polytetrafluoroethylene (PTFE), ethylene tetrafluoroethylene (ETFE), fluorinated ethylene propylene (FEP), polyoxymethylene (POM), polybutylene terephthalate (PBT), polyether-block-ester, polyvinylchloride (PVC), polyether-block-amide, polyetheretherketone (PEEK), polyimide (PI), polyphenylene sulfide (PPS), polyphenylene oxide (PPO), poly(ethylene naphthalenedicarboxylate) (PEN), polysulfone, perfluoro(propyl vinyl ether) (PFA), or mixtures, combinations, copolymers thereof, and the like.

The inflatable balloon will typically have a length of at least 1 cm to 50 cm, preferably being in a range from about 1.5 cm to 20 cm, and may have inflated diameters in a range from 1.5 mm to about 20 mm, for instance 1.5 mm to 5 mm, but may be of any suitable size.

An inflatable balloon catheter comprising a coated inflatable balloon as described herein may be used for any suitable purpose. In preferred embodiments, the inflatable balloon catheter is an intravascular inflatable balloon catheter. For example, the inflatable balloon catheter may be an angioplasty catheter or a stent delivery catheter. Preferably, the inflatable balloon catheter is an angioplasty catheter. Preferably, the inflatable balloon catheter is used for treatment of restenosis in an artery.

In use, the inflatable balloon may be inflated by infusing fluid, such as water, saline or the like, into the inflatable balloon through, for example, a lumen of a catheter in communication with the interior surface of the inflatable balloon.

Any suitable implantable medical stent may be coated with a nanoparticle or microparticle coating described herein. The sent may comprise a frame comprising one or more of a variety of biocompatible metals such as stainless steel, titanium, magnesium, aluminum, chromium, cobalt, nickel, gold, iron, iridium, chromium/titanium alloys, chromium/nickel alloys, chromium/cobalt alloys, such as MP35N and L605, cobalt/titanium alloys, nickel/titanium alloys, such as nitinol, platinum, and platinum-tungsten alloys. The metal composition gives the stent framework the mechanical strength to support the lumen wall of the vessel and sufficient longitudinal flexibility so that it can be transported through the cardiovascular system.

The stent may comprise a polymeric frame that may be biodegradable, biostable, or comprise a mixture of polymeric materials that are both biostable and biodegradable. Biodegradable polymers appropriate for the stents include polylactic acid, polyglycolic acid, and their copolymers, caproic acid, polyethylene glycol, polyanhydrides, polyacetates, polycaprolactones, poly(orthoesters), polyamides, polyurethanes and other suitable polymers. Biostable polymers appropriate for the stents include polyethylene, polypropylene, polymethyl methacrylate, polyesters, polyamides, polyurethanes, polytetrafluoroethylene (PTFE), polyvinyl alcohol, and other suitable polymers. These polymers may be used alone or in various combinations to give the stent unique properties such as controlled rates of degradation.

The stent frame may be formed by shaping a metallic wire or polymeric filament, or by laser cutting the stent from a metallic or polymeric sheet, or any other appropriate method. The surface of the stent framework may be cleaned by washing with surfactants to remove oils, mechanical polishing, electropolishing, etching with acid or base, or any other effective means to expose a clean, uniform surface that is ready for applying a coating The coating may include a polymer matrix comprising biodegradable polymers such as polylactic acid, polyglycolic acid, and their copolymers, caproic acid, polyethylene glycol, polyanhydrides, polyacetates, polycaprolactones, poly(orthoesters), polyamides, polyurethanes and other suitable polymers. The therapeutic agent-containing nanoparticles or microparticles may be incorporated within the polymeric matrix, applied to the polymeric matrix, or the like. The coating may comprise one or more layer, such as described above.

The stent may be balloon-expandable or self-expanding. The coated stent may be positioned within a vessel through the use of a catheter to which the stent is coupled. The catheter may comprise an inflatable balloon that may be inflated to expand the stent such that the stent contacts a wall of the vessel, the balloon may be deflated, and the catheter removed leaving the stent in place. The catheter may include a sheath that retracts to allow expansion of a self-expanding stent to contact a wall of the vessel. When the sheath is fully retracted, the catheter may be removed from the vessel, leaving the stent in place.

Referring now to FIG. 1, a sectional view of a medical device 400 is shown. The medical device 400 comprises a body 410 having exterior surface 404. A coating 200 is disposed on the exterior surface 404 of the medical device 400. The coating 200 comprises a therapeutic agent-containing nanoparticle or microparticle and may optionally comprise one or more polymers to assist in controlling the release of the nanoparticles or microparticles or protecting the nanoparticles or microparticles during the delivery process (such as navigating the device through the vasculature). The coating 200 may comprise one or more additional layers (not shown). The body 410 may define an interior surface 102 defining an interior space 105. The device 400 may be or comprise an inflatable balloon or a stent.

Figure 2:
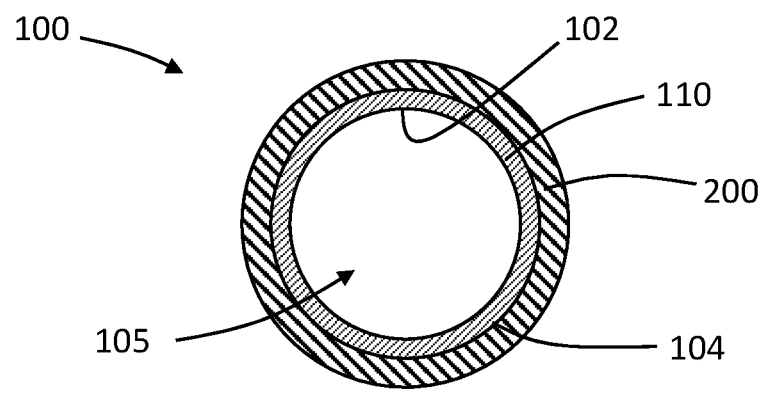
FIG. 2 is a schematic sectional view of an embodiment of an inflatable balloon having a coating comprising a nanoparticle or microparticle for releasing a therapeutic agent.

Referring now to FIG. 2, a sectional view of an inflated inflatable balloon 100 is shown. The inflatable balloon 100 comprises a wall 110 defining an interior surface 102 and an exterior surface 104, the interior surface 104 defining an interior space 105. A coating 200 is disposed on the exterior surface 104 of the inflatable balloon 100. The coating 200 comprises a therapeutic agent-containing nanoparticle or microparticle and may optionally comprise one or more polymers to assist in controlling the release of the nanoparticles or microparticles or protecting the nanoparticles or microparticles during the delivery process (such as navigating the balloon through the vasculature). The coating 200 may comprise one or more additional layers (not shown).

Figure 3:
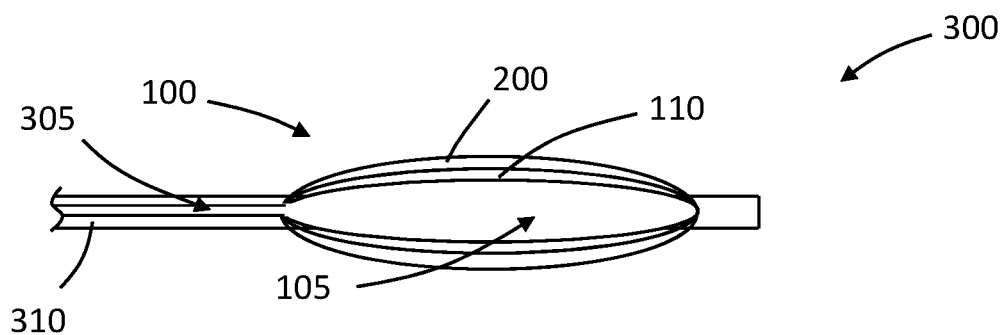
FIG. 3 is a schematic sectional view of an inflatable balloon catheter in accordance with various embodiments described herein.

Referring now to FIG. 3, a sectional view of an inflatable balloon catheter 300 is shown. The inflatable balloon catheter 300 includes a catheter 310 and an inflatable balloon 100 having a wall 110 defining an interior surface 102 and an exterior surface 104 (as shown in FIG. 2), the interior surface 102 defining an interior space 105. A coating 200, such as a coating described above regarding FIG. 2 is disposed on the exterior surface 104 defined by the inflatable balloon wall 110. The catheter 310 defines a lumen 305 in communication with the interior space 105 of the inflatable balloon 100 for inflating the inflatable balloon 100.

Figure 4A:
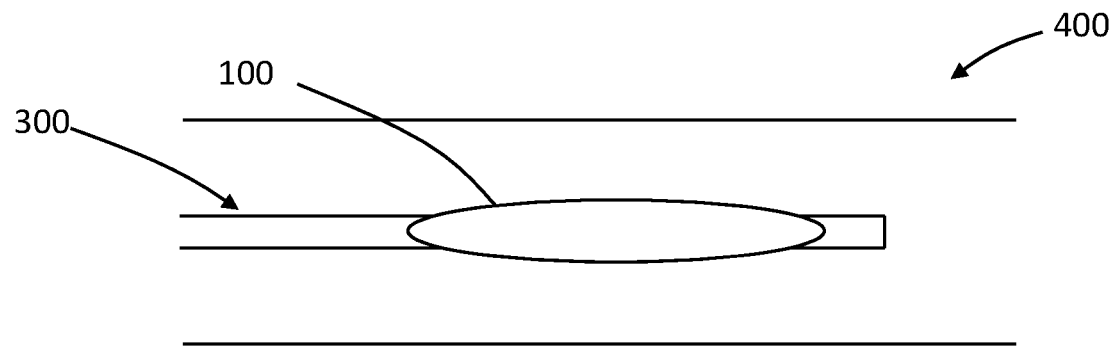
FIGS. 4A-B are schematic views of an inflatable balloon catheter in an artery in uninflated (FIG. 4A) and inflated (FIG. 4B) states in accordance with various embodiments described herein.
Figure 4B:
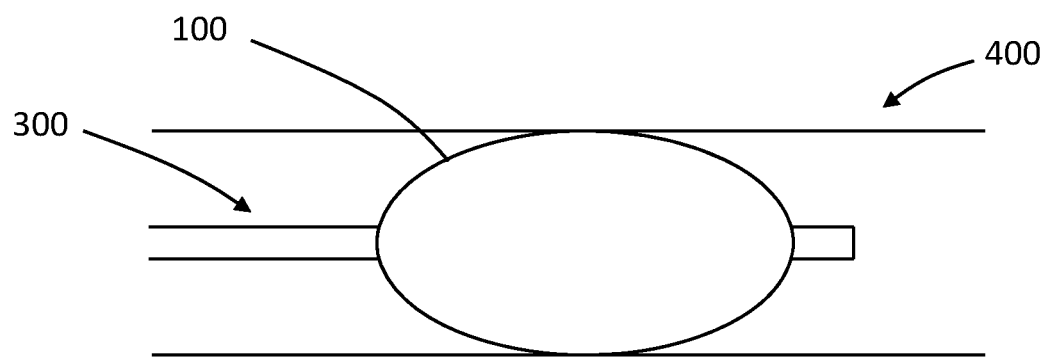

Referring now to FIGS. 4A-B, schematic drawings showing an inflatable balloon catheter 300 in a vessel 400 in uninflated (FIG. 4A) and inflated (FIG. 4B) states are shown. The inflatable balloon catheter 300 may be advanced within the vessel 400, such as an artery, until inflatable balloon 100 is aligned with a target site for intervention, such as a narrowing of the artery 400. The inflatable balloon 100 may be inflated (FIG. 4B) with fluid. Contact of the coating (not shown) disposed on the balloon with a wall of the artery 400 results in transfer of the coating 200 having the nanoparticles or microparticles from the balloon 100 to the wall of the artery 400.

Figure 5:
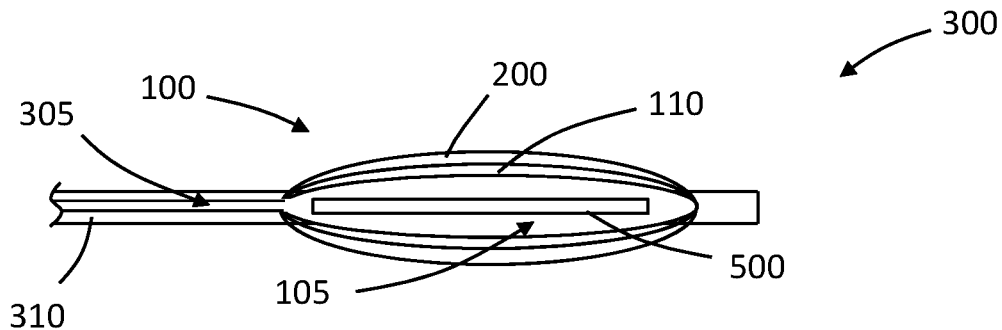
FIG. 5 is a schematic sectional view of an inflatable balloon catheter having an electromagnet in accordance with various embodiments described herein.

FIG. 5 is a sectional view of an inflatable balloon catheter 300 similar to the inflatable balloon catheter 300 depicted in FIG. 3. For numbered elements depicted in FIG. 5 that are not specifically discussed, reference is made to the description above regarding FIG. 3. The inflatable balloon catheter 300 depicted in FIG. 5 includes an electromagnet 500. The electromagnet 500 may be activatable by applying a current. The current may be applied by a power source (not shown), which may be activatable by a switch (not shown).

The coating 200 may comprise nanoparticles or microparticles that include a magnetic particle. When the electromagnet 500 is activated, the nanoparticles or microparticles in the coating 200 may be attracted to the electromagnet 500 and thus may be retained on the exterior surface of the wall 110 of the balloon 100 when the catheter 300 is tracked through the vasculature of a patient. When the balloon 100 is positioned in a target location of the vasculature, the electromagnetic may be deactivated (either before or after inflation of the balloon) to release the nanoparticles or microparticles.

Figure 6:
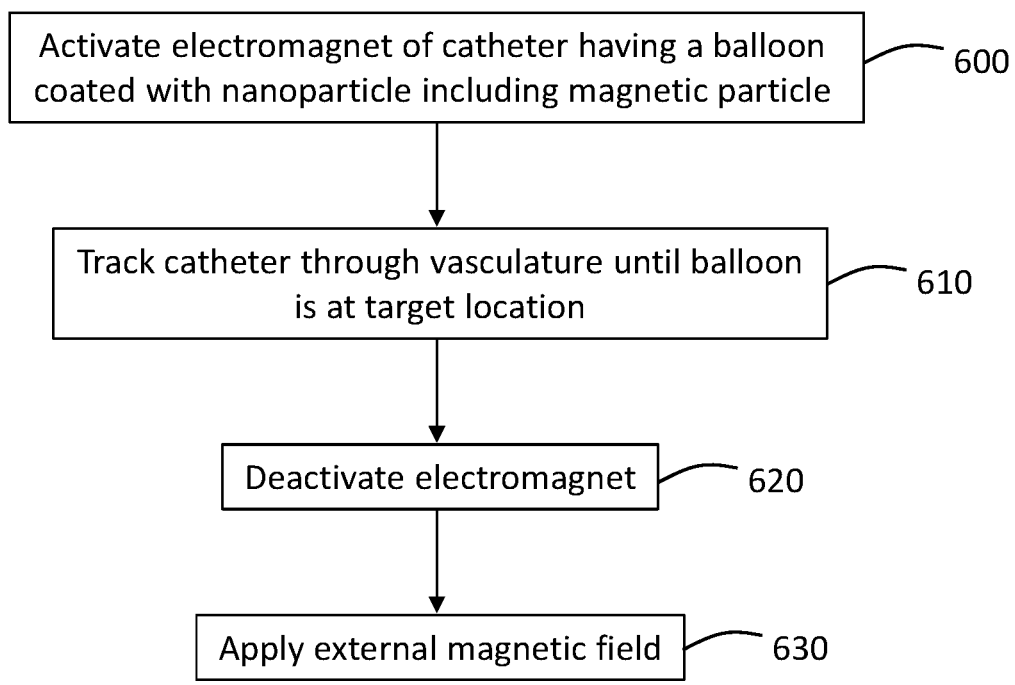
FIG. 6 is a flow diagram of a method in accordance with various embodiments described herein.

FIG. 6 depicts a flow diagram of a method that may be employed with, for example, an inflatable balloon catheter 300 depicted in FIG. 5. The method includes activating an electromagnet of catheter having an inflatable balloon coated with nanoparticle or microparticle including a magnetic particle (600) and tracking the catheter through vasculature until balloon is at target location (610). The electromagnet may be deactivated (620) to release the nanoparticles or microparticles at the target location. The method may optionally include applying an external magnetic field (630) to cause the nanoparticles or microparticles to move towards a tissue location, such as an inner surface of the vessel wall. By "external magnetic field," it is meant that the source of the magnetic field is external to the patient.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising" and the like.

Thus, embodiments of THERAPEUTIC PARTICLES FOR TREATING VASCULAR DISEASES are disclosed. One skilled in the art will appreciate that the nanoparticles or microparticles and methods described herein can be practiced with embodiments other than those disclosed. The disclosed embodiments are presented for purposes of illustration and not limitation.

What is claimed is:
1. A medical device comprising:
a body having an exterior surface, wherein the body is configured to be inserted into a patient's vasculature;
a coating disposed on the exterior surface of the body, the coating comprising a first nanoparticle or microparticle, wherein the nanoparticle or microparticle comprises:
a core comprising a biodegradable polymer;
an exterior comprising hydrophilic moieties;
a magnetic particle; and
a therapeutic agent; and
an electromagnet, wherein the electromagnet attracts the first nanoparticle or microparticle when the electromagnet is activated, and wherein the electromagnet is positioned to retain the first nanoparticle or microparticle on the exterior surface of the body when the electromagnet is activated, wherein the coating is on the exterior surface of the body prior to insertion of the body into the patient's vasculature.

2. The medical device of claim 1, wherein the biodegradable polymer comprises poly(lactic-co-glycolic acid) (PLGA).

3. The medical device of claim 1, wherein the hydrophilic moieties comprise polyethylene glycol (PEG) or a polysaccharide.

4. The medical device of claim 1, further comprising a lipid monolayer.

5. The medical device of claim 4, wherein the lipid monolayer comprises the hydrophilic moiety.

6. The medical device of claim 1, wherein the therapeutic agent is selected from the group consisting of an anti-restenosis agent, an anti-proliferative agent, a thrombolytic agent, and an anti-inflammatory agent.

7. The medical device of claim 1, wherein the first nanoparticle or microparticle further comprises a targeting moiety that targets the nanoparticle or microparticle to an arterial lesion.

8. The medical device of claim 7, wherein the targeting moiety comprises a moiety that targets the nanoparticle or microparticle to activated platelets.

9. The medical device of claim 7, wherein the targeting moiety comprises fucoidan.

10. The medical device of claim 7, wherein the targeting moiety comprises a moiety that targets the nanoparticle or microparticle to collagen.

11. The medical device of claim 7, wherein the targeting moiety comprises DS-SILY.

12. The medical device of claim 7, wherein the targeting moiety comprises a moiety that targets the nanoparticle or microparticle to fibrin.

13. The medical device of claim 7, wherein the targeting moiety comprises CREKA.

14. The medical device of claim 1, wherein the coating comprises a second nanoparticle or microparticle, wherein the second nanoparticle or microparticle comprises a therapeutic agent different from the therapeutic agent of the first nanoparticle or microparticle.

15. The medical device of claim 14, wherein the second nanoparticle or microparticle biodegrades more quickly than the first nanoparticle or microparticle.

16. The medical device of claim 1, wherein the body comprises a stent or a balloon.

17. A method comprising:
providing the medical device of claim 1;
activating the electromagnet of the device;
tracking the device through a vasculature of a patient until the first nanoparticle or microparticle is located at a target location; and
deactivating the electromagnet when the first nanoparticle or microparticle is located at a target location.

18. The method of claim 17, further comprising applying an external magnetic field to direct the nanoparticle or microparticles to a predetermined location in the patient.

19. A method comprising:
providing the medical device of claim 1;
inserting the medical device in a target location of a patient; and
contacting the medical device to tissue at the target location, wherein contacting the medical device to the tissue causes the nanoparticle or microparticle to be transferred to the tissue.

20. The method of claim 19, wherein the tissue of the patient to which the nanoparticle or microparticle is transferred is a wall of an artery.

21. A medical device comprising:
an inflatable balloon having an exterior surface, wherein the inflatable balloon is configured to be inserted in a patient's vasculature;
a first nanoparticle or microparticle disposed on the exterior surface of the balloon, the first nanoparticle or microparticle comprising a magnetic particle and a therapeutic agent; and
an electromagnet, wherein the electromagnet attracts the first nanoparticle or microparticle when the electromagnet is activated, and wherein the electromagnet is positioned to retain the first nanoparticle or microparticle on the exterior surface of the balloon when the electromagnet is activated,
wherein the coating is on the exterior surface of the inflatable balloon prior to insertion of the body into the patient's vasculature.

* * * * *